United States Patent [19]

Hudson et al.

[11] Patent Number: 4,636,572

[45] Date of Patent: Jan. 13, 1987

[54] PERMEABILITY CONTRAST CORRECTION EMPLOYING PROPIONATE-SEQUESTERED CHROMIUM(III) PREPARED BY NITRITE/DICHROMATE REDOX

[75] Inventors: Paul S. Hudson; Tod K. Shioyama, both of Bartlesville, Okla.

[73] Assignee: Phillips Petroleum Company, Bartlesville, Okla.

[21] Appl. No.: 710,755

[22] Filed: Mar. 11, 1985

[51] Int. Cl.$^4$ ............................................. C07F 11/00
[52] U.S. Cl. ........................................ 556/2; 556/5; 556/6; 556/61; 556/4; 252/8.55
[58] Field of Search ................... 556/61, 4, 2, 5, 6

[56] References Cited

U.S. PATENT DOCUMENTS

| | | |
|---|---|---|
| 2,470,378 | 5/1949 | Skala ............................ 556/61 X |
| 2,615,031 | 10/1952 | Stover . |
| 2,650,239 | 8/1953 | Stover . |
| 2,678,328 | 5/1954 | Drew . |
| 3,193,398 | 7/1965 | Iannicelli . |
| 3,256,266 | 6/1966 | Burt . |
| 3,462,496 | 8/1969 | Fletcher et al. . |
| 3,705,183 | 12/1972 | Bunger et al. ................. 556/61 X |
| 3,714,211 | 1/1973 | Erdmann et al. . |
| 3,845,822 | 11/1974 | Clampitt et al. . |
| 3,900,689 | 8/1975 | Deyrup . |
| 3,926,258 | 12/1975 | Hessert et al. . |
| 3,932,285 | 1/1976 | Ceprini et al. .................... 556/61 X |
| 3,959,093 | 5/1976 | Merkl . |
| 4,488,601 | 12/1984 | Hammett . |

OTHER PUBLICATIONS

Chemical Abstracts, vol. 66, 25561j (1967).
Chemical Abstracts, vol. 83, 169154c (1975).
Chemical Abstracts, vol. 97, 151613f (1982).
Chemical Abstracts, vol. 73, 70366e (1970).
Chemical Abstracts, vol. 95, 139641q (1981).
Chemical Abstracts, vol. 87, 142053q (1977).
Chemical Abstracts, 74, 23649k (1971).

*Primary Examiner*—Helen M. S. Sneed
*Attorney, Agent, or Firm*—French and Doescher

[57] ABSTRACT

A process for preparing clear green chromium(III) propionate solutions which comprises admixing such as propionic acid with water, a chromium(VI) source such as dichromate, adding thereto a nitrite, such as sodium nitrite, to reduce the chromium(VI) to chromium(III), in the presence of excess acid, preferably propionic acid, optionally combined with additional acid such as muriatic acid, to produce a stable solution useful with polymers, such as partially hydrolyzed acrylamide-based polymers, in permeability contrast correction procedures for high permeability streaks in oil field treatments.

19 Claims, 2 Drawing Figures

PERMEABILITY CONTRAST CORRECTION EMPLOYING PROPIONATE-SEQUESTERED CHROMIUM(III) PREPARED BY NITRITE/DICHROMATE REDOX

FIELD OF THE INVENTION

The invention pertains to methods of preparing stable propionate-sequestered chromium(III) aqueous solutions. In a particular aspect, the invention pertains to the use of a nitrite/dichromate redox system to prepare propionate-sequestered chromium(III) solutions. In a related aspect, the invention pertains to a method of mixing for improved preparations of propionate-sequestered chromium(III) solutions. The invention further pertains to methods for correcting the water permeability contrast of heterogeneous subterranean formations.

BACKGROUND OF THE INVENTION

In oil-producing fields employing waterflooding, the water tends to channel through zones of high permeability and tends to by-pass a large amount of oil-in-place. Since waterflooding fluids usually contain chemicals, and even small amounts of chemicals in the hundreds of millions of gallons of water employed becomes expensive, an efficient sweep of the waterflood is important. If high permeability water channels can be blocked, the water is diverted into tighter oil-bearing zones.

Water channeling can be reduced by injecting a solution of a polymer with a polyvalent metal crosslinking agent under conditions which gel the polymer, plugging off the more permeable formation, and diverting the subsequently injected floodwater into the formerly less permeable but now relatively more permeable oil bearing zones. The use of aluminum citrate and related polyvalent metal cations as crosslinking agents has been known for some time. However, the citrate-sequestered aluminum type of agents has not been entirely satisfactory in some of the more hostile environments, such as formation temperatures of greater than about 170° F. and/or hardness cation values in the formation water of greater than about 500 ppm.

Chromium(III) propionate solution is an effective agent for crosslinking such as the partially hydrolyzed acrylamide-based polymers to form a gel in high permeability zones of an oil bearing reservoir, in either near well treatments or indepth applications. Not only is a chromium(III) propionate solution effective for such permeability correction processes, and useful in hard brines, but surprisingly the propionate component is biocidal against the pestiferous sulfate-reducing bacteria usually present in the formation water. Thus, both the crosslinking benefits can be obtained plus the biocidal benefits.

However, the chromium(III) propionate solution must be discretely prepared. Redox methods resulting in sulfate in the product are undesirable because of potential formation damage caused by precipitation of BaSO$_4$ and/or CaSO$_4$, and since sulfate can be metabolized by sulfate-reducing bacteria to produce corrosive "souring" gas H$_2$S.

Solutions of chromium(III) propionate of good clarity easily and readily prepared in a reproducible manner have been a goal, or perhaps an obstacle, in the path of the use of this highly important material in oil field processes.

BRIEF DESCRIPTION OF THE INVENTION

We have discovered that the use of a nitrite in reducing a chromate or dichromate in admixture with a propionic acid source and water, employing particular proportions, results consistently in a clean clear green chromium(III) propionate solution, a propionate-sequestered chromium(III). We have discovered that it requires at least about a 4:1 mole ratio of propionate:chromium to ensure a proper chromium(III) propionate solution, and further that an excess of acid (ligand) is necessary so as to have a total ligand:chromium mole ratio on the order of at least about 11:1.

We also have discovered that this needed excess ligand acidity can be replaced by a less expensive acid, such as acetic acid or muriatic acid, if employed after the chromium(III) propionate complex solution is first formed, and thus achieve a stable solution at lesser cost.

In fact, the latter-prepared mixed-ligand material, we have found, is preferred for near-well treatments since it tends to gel more quickly, though it is also suitable for indepth crosslinking applications. The higher propionate-containing solutions presently are preferred for the indepth crosslinking applications since they tend to take longer to effect gelling of the polymer, though also are useful for near-well treatment procedures.

We have further discovered a preparative mixing method employing a circulating loop system which approximately halves the time otherwise required for regular batch-stirring preparative processes.

It is an object of our invention to prepare chromium(III) propionate complex solutions useful for gelling water-soluble polymeric viscosifiers. It is a further object of our invention to prepare propionate-sequestere chromium(III) solutions of effective character, uniform, clear, without sludge content. It is also an object of our invention to provide improved methods of permeability contrast correction in high permeability streaks both for indepth crosslinking applications and for near-well applications. A further object of our invention is to provide a method to produce propionate-sequestered chromium(III) solutions in stable as well as economical form. An additional object of our invention is to provide a method for treating an underground formation employing a gelable injectable liquid composition.

BRIEF DESCRIPTION OF THE DRAWING

Spectrum (1) is that of a solution resulting from the reaction system of dichromate, nitrite, propionic acid, and water, according to the present invention.

Spectrum (2) is that of a solution resulting from the reaction system of dichromate, bisulfite, propionic acid, and water. This solution of propionate-sequestered chromium(III) was satisfactory, except for the co-production of sulfate.

Spectrum (3) is that of a solution resulting from the reaction system of dichromate, nitrite, propionic acid, water, and muriatic acid, using a preparative mode in accordance with one aspect of our invention.

Spectrum (4) is that of a solution resulting from the use of a preparative mode employing chromium(III) nitrate, propionic acid, water, and propionic anhydride. It would appear chemically satisfactory, except that the high cost of the chromium(III) nitrate makes it unattractive on a commercially practical basis.

Spectrum (5) is that of a solution resulting from a preparative mode employing potassium dichromate, water, and propanal, with very unsatisfactory results in a non-useful product.

DETAILED DESCRIPTION OF THE INVENTION

In producing the propionate-sequestered chromium-(III) solutions in accordance with our invention, several components are employed: (1) a chromium(VI) component, (2) a nitrite component, (3) a ligand selected from (a) a propionic acid source and (b) a propionic acid source with further acid which can be such as a mineral acid or acetic acid, and (4) water.

The molar ratio of ligand:chromium should be at least about 4:1 to ensure the formation of suitable chromium-(III) propionate solution. Preferably, about an 11:1 ligand:chromium molar ratio should be used in order to maintain a stable chromium complex in solution. The difference of about 7:1 molar ratio of the required level of formation of propionate ligand:chromium of at least about 4:1 and the stabilizing level of about 11:1 can be provided by an additional acid ligand such as, e.g., aqueous hydrochloric acid or acetic acid. In near-well treatments, the use of the additional acid ligand is preferred; in other instances, e.g., indepth crosslinking applications, it is generally preferred to use the at least about 11:1 ligand:chromium molar ratio in which the ligand is exclusively propionic acid.

Chromium(VI) Component

The chromium(VI) component is selected from chromium(VI) oxide, and preferably from any of the alkali metal or ammonium dichromates or chromates. Presently preferred is sodium dichromate dihydrate because of availability and economy. There is no particular difference whether the chromium(VI) component is chromate or dichromate since in acidic solutions the chromate in any event is converted to dichromate. Whenever chromate is employed, then additional amounts of the propionic acid source are accordingly required and are readily calculated.

Nitrite Component

The nitrite component is selected from any of the alkali metal or ammonium nitrites; presently preferred is sodium nitrite for convenience, availability, and economy.

Acid Propionate Source

The propionic acid ligand source is selected from propionic acid and propionic acid anhydride. The propionic anhydride forms propionic acid upon adequate dilution with water.

Water

Water is required to make the admixtures. In order of preference suitable water includes demineralized water, zeolite softened water, fresh water, and sodium chloride brine. The water employed should be a clear water, avoiding sediment-containing waters, not so much that such will interfere in the preparation of suitable chromium(III) propionate solutions, but rather that sediments may interfere with the suitability of the solution as hereinafter described since injected solids can cause formation damage in subterranean strata.

Optional Additional Acids

The additional acid component can be selected from any of the mineral acids, acetic acid, acetic anhydride, and propionyl and acetyl halides such as propionyl chloride and acetyl chloride. Mineral acids include such as muriatic (hydrochloric) acid, hydrobromic acid, phosphoric acid, and sulfuric acid, including mixtures. Presently, muriatic acid is preferred for convenience, availability, and economy. Sulfuric acid, while operable, is to be avoided since it adds sulfates to the liquor, which are objectionable in connate barium-containing water, and also to some extent objectionable in calcium containing waters because of the formation of insoluble sulfates. Sulfates can be metabolized by sulfate-reducing bacteria. Phosphoric acid, while operable, also is to be avoided since it is objectionable in calcium-containing connate waters due to the formation of insoluble phosphates.

Acetic acid, phosphoric acid, and sulfuric acid, each can be obtained in varying strengths up to 100 percent. With these, the added acid can be readily calculated. Hydrochloric acid (muriatic acid) is commercially obtainable as a moderately concentrated aqueous solution in various grades of 28 to 37 percent hydrochloric acid (hydrogen chloride), so allowance must be made for the additional water involved. One reason for using the hydrochloric acid or acetic acid is simply that the reagents are much cheaper than is propionic acid. At the same time, the solutions containing the additional acid have been found by us to be preferred for near-well treatment, according to our investigations, while the compositions with higher concentrations of propionic acid presently are preferred for indepth strata work.

Reactant Component Ratios

The propionic acid source should be diluted somewhat with water to form a moderately dilute solution of propionic acid suitable for dissolving the nitrite source and chromium(VI) source therein for solubility and reactivity purposes. Approximately 10 molar aqueous propionic acid, e.g., is suggested as suitable and convenient for use in our invention. Suggested is the addition of sufficient water to the propionic acid source to produce a molarity of about 10 molar propionic acid or less, such as about 6 to 10 molar, more usually about 6.5 to 9.5 molar. Assuming the density of an aqueous propionic acid solution to be approximately 1 gram per mL, the preferred range represents about a 50:50 to 70:30 weight:weight propionic acid:water admixture range.

The latter concentration was used in many of the experimental runs hereinafter described.

Sufficient nitrite source should be employed so as to reduce the chromium(VI) source completely to chromium(III). Preferably, a small stoichiometric excess of nitrite source is employed relative to the chromium(VI) source. Presently recommended is a molar ratio of at least about 3:1 nitrite:dichromate; presently preferred is a molar ratio of at least about 3.5:1 nitrite:dichromate. Excess nitrite above this level is not detrimental, but simply appears unnecessary at the present time. However, sufficient nitrite should be employed so as to ensure the complete reduction of chromium(VI), since residual dichromate is detrimental to polymer gel stability in applications wherein the chromium(III) propionate solution is used to gel polymers for permeability contrast correction is enhanced oil recovery operations.

An effective molar ratio of propionate:chromium should be employed in order to effectuate the formation of a suitable chromium(III) propionate solution. It presently is considered that a molar ratio of at least about 4:1 propionic acid:chromium is required to form the complex itself in solution.

Figure 2:
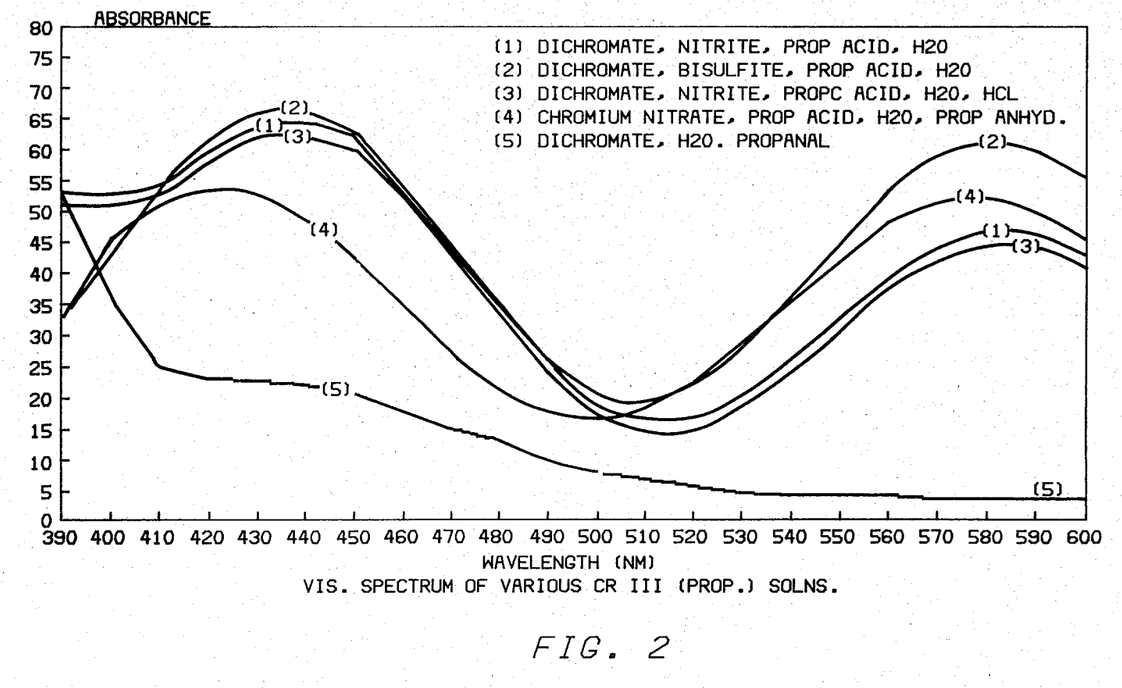
FIG. 2 presents the spectra of solutions of materials resulting from several different preparative routes for the attempted preparation of active chromium(III) propionate solutions. The spectra shown are in the visible range of 390 to 600 nm wavelength numbers. Active chromium(III) propionate has absorbance maxima at about 435 nm and 580 nm.

The process/reaction appears to be much more than the simple formation of what might be viewed as a simple chemical compound chromium(III) propionate which conventionally would be considered to be represented by $Cr(propionate)_3$. Rather, employing reagents, proportions, reaction times, temperatures, as recommended, a stable clear green solution of a complex is obtained which has a characteristic spectrum as described hereinabove with respect to FIG. 2.

In order to maintain the desired complex, more than the minimum complexing ratio of about 4 moles of propionic acid ligand:chromium is required. A total ligand concentration of at least about a molar ratio of 11:1 acid:chromium provides needed additional excess stabilizing acidity. As is discussed hereinbelow, some of this excess acidity can be replaced or substituted by acids cheaper than propionic acid such as aqueous hydrochloric acid. Excess propionic or other acid above the 11:1 ratio is not objectionable.

Presently suggested is a broad ratio of such as about 4:1 to such as about 60:1 molar ratio of propionic acid to chromium, presently preferred about 4:1 to 45:1. In a number of our developmental runs it was established that the weight:weight ratio of the 70:30 weight:weight propionic acid:water admixture to potassium dichromate should not be much less than about 7.7 to 1, which translates to a molar ratio of about 10.7 to 1 propionic acid:chromium(VI). This could also be expressed as about 21.4 moles propionic acid per mole of $K_2Cr_2O_7$.

In the embodiment of our invention involving the use of an additional acid in place of some of the propionic acid ligand, the chromium(III) propionate solution is first formed using the above-indicated minimum amounts of propionic acid. Thereafter, the additional acid source is added to the chromium(III) propionate reaction solution so that the ultimate solution mixture contains the desired total ligand:chromium ratio as discussed.

After all of the reactants/reagents have been admixed together, a sufficient time should be allowed in order to provide a suitable digestion reaction. The reaction temperature employed should be controlled so as to avoid excessively high reaction temperatures. A suitable effective time and temperature of reaction should be employed so as to produce the desired chromium(III) propionate solution. Presently suggested are reaction times on the order of about 0.5 to 24 hours, presently preferred about 1 to 4 hours; with reaction temperatures of about 60° C. to 100° C., presently preferred about 70° C. to 90° C. There seems to be a relationship between a need for longer reaction times at lower reaction temperatures, particularly at the lower end of the reactant concentration ranges, whereas somewhat lower reaction temperatures and shorter reaction times are suitable for somewhat higher reactant concentrations. In general, the digestion period needed is shorter at the upper end of the reaction temperature range, as might be expected in most chemical reactions. Times greater than 24 hours can be employed for the reaction or digestion, though such are not considered necessary since the reactions generally are essentially complete within 24 hours at reasonable temperatures within the designated reaction temperature ranges and at reasonable or practical concentrations within the designated molar ratio ranges of reactants.

The sequence of reactant addition should be followed with reasonable care. Generally, the propionic acid source is first diluted with water to the recommended molar concentration of propionic acid. To this is added, with stirring, the chromium(VI) source until this is thoroughly admixed and dissolved. Heating should be applied in order to obtain appropriate solution temperatures. Alternatively, the dichromate is dissolved in water, and the propionic acid added thereto. To the three-component system of propionic acid/water/chromium (VI) then is added, slowly, with stirring, the nitrite source.

After the recommended amounts are admixed, the admixture is maintained within the suggested temperature range for the desired reaction time. The product obtained is an aqueous homogeneous green solution of propionate-sequestered Cr(III). With recommended components and ratios, temperatures, and digestion times, there is no residual dichromate, no sediment or brown sludge, and a single phase reaction system is involved.

Figure 1:
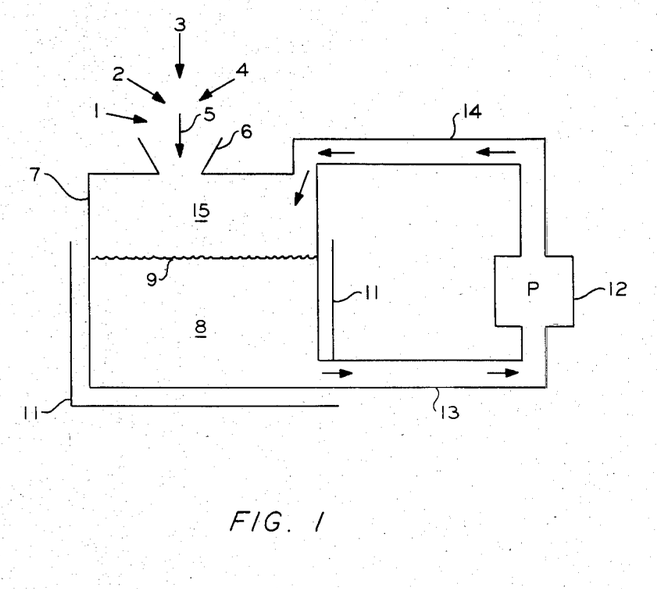
FIG. 1 illustrates a preferred method of mixing the preparative ingredients to form the solution of the chromium(III) propionate-sequestered complex. Chromium(VI) compound 1, nitrite 2, acid 3, and water 4, are added 5 through opening 6 to mixing vessel 7 to form admixture 8, with fill or level line shown as 9. Heating/cooling 11 controls mixture temperature. Loop circulating pump 12 provides mixing by taking admixture out 13 and returning 14. A free-board 15 is maintained to avoid overfilling and splash-out.

In the process of preparing our water-soluble propionate-sequestered chromium(III) solutions, the reaction or digestion time, we have found, can be substantially reduced by the use of a loop-type circulating reactor. The digestion period employing the circulating pump loop reactor is about 50 percent shorter than the observed digestion period required in a stirred batch reactor. A simplified version of such a circulating reactor is shown in the attached drawing as FIG. 1.

Dilution

The resulting acid-ligand chromium(III) solution can be used as prepared. The as-prepared stable solutions of our invention can be held or stored indefinitely, preferably in closed corrosion-resistant drums.

The stable solutions can be diluted, if desired, with water prior to use so as to provide greater volumes for easier metering and mixing for use in water channeling control applications.

Dilution preferably is with soft or fresh water. The extent of dilution can be as convenient, though up to a maximum of about 1 part solution:100 parts water by volume is suggested to avoid possible loss of stability.

Partial Neutralization

The resulting acid-ligand chromium(III) solution, with or without dilution, is relatively acidic. The solutions are particularly acidic in the inventive aspect using a proportion of added acid in which the added acid is a strong acid such as muriatic acid, rather than all propionic acid. Thus, the solutions may tend to be relatively corrosive to some metals due to the inherent acidity.

The acid-ligand chromium(III) solutions can be partially neutralized, if desired, particularly if the solutions are to be held for a time prior to usage, as well as to minimize potential acidic-type corrosion of pumping equipment and lines in treatment of oil-bearing formations.

The pH of the acid-ligand chromium(III) solutions can be raised up to such as about 3-5, more preferably about 3-4, by use of an alkaline agent such as ammonia, ammonium hydroxide or an alkali metal hydroxide such as sodium hydroxide. Alkali metal carbonates can be used, but the consequent effervescence of carbon dioxide poses obvious problems in handling.

The alkaline agent preferably is diluted with water and added slowly with stirring to the acid ligand-chromium(III) solution. The pH can be monitored for control purposes.

EXAMPLES

Examples provided are intended to assist one skilled in the art to a further understanding of our invention. Particular materials employed should be considered as exemplary and not limitative. The Examples are part of our disclosure. The specification including text, Examples, data, and claims, should be viewed as a whole in considering the reasonable and proper scope of our invention.

Working Examples

Experimental runs (Example I) were carried out initially on a laboratory scale in a 500 mL glass reactor, and then scaled-up successfully in a five-gallon glass reactor (Example II). Example IV describes a further scaled-up run carried out in a 100-gallon reactor.

In the laboratory scale runs, a 500 mL 3-necked round-bottomed flask was used. This vessel was equipped with a variable speed mechanical stirrer, a water-cooled reflux condenser, and a thermocouple probe for determining the temperature of the reaction mixture. A heating mantle was used as necessary to supply heat to the reactor contents.

Generally, the aqueous propionic acid was charged to the reactor, and the designated amount of dichromate was added and dissolved at ambient temperature with stirring. The sodium nitrite then was added in portions either as a solid or as small volume aliquots of an aqueous $NaNO_2$ solution. Each addition was carried out slowly with stirring and cooling if necessary so that the temperature of the reaction mixture did not exceed 70° C. and so that no toxic oxides of nitrogen were liberated. After all of the reactants were added, the stirred mixture was heated to a specified temperature for a designated time period.

At the end of the reaction period, the solution was cooled to ambient temperature and checked for residual dichromate. In the residual dichromate test, a small sample of the reaction mass was contacted with one to two drops of a 0.1M barium chloride solution. The appearance of a yellow-white precipitate signaled the presence of residual dichromate and the product mixture was considered unacceptable for crosslinking (gelling) polymeric viscosifiers in enhanced oil recovery operations. Residual dichromate in such gels can cause polymer degradation.

The reaction mixture also was checked for the presence of water-insoluble polymeric species. The exact chemical nature of these species is not known, however, such species may be polymeric aggregates containing chromium and propionic acid units. In this test, a small sample of the reaction mass was diluted with distilled water. The appearance of a white film or skin on the surface of the liquid or on the sides of the beaker signaled the presence of polymeric species. The appearance of this water-insoluble material rendered the product mixture unacceptable for use in enhanced oil recovery operations because the presence of insolubles could give rise to injectivity problems.

The reaction mass also was characterized by visible spectral analysis. A sample was scanned over the visible spectrum between 390 nm and 600 nm on a Perkin Elmer 530 UV-Visible Spectrophotometer. Those samples exhibiting maximum absorbance peaks at 435 nm and 580 nm were found to be suitable for crosslinking (gelling) polymeric viscosifiers for use in enhanced oil recovery operations. See FIG. 2 herewith.

In this work, samples of the reaction mass were checked for the presence of residual dichromate, water-insoluble polymeric species, and characterized by visible analysis before any bulk gels or core tests were carried out. Suitable product masses were transparent, dark green-colored solutions which contained no solids, and with which no solids were produced on dilution of these mixtures with water.

Example I

This Example presents typical laboratory runs which produced "active" chromium(III) propionate solutions. These product solutions contained no residual dichromate and produced no insoluble material when diluted with water. The visible spectra of these "active" solutions exhibited absorbance maxima at 435 nm and 580 nm. These solutions gelled polyacrylamide solutions in bulk gel tests. The use of these solutions in Berea sandstone core runs, even in the presence of hard brines, such as South Burbank Unit brine, resulted in the development of high residual resistance factors (RRF). For example, the sequential injection of polyacrylamide-brine-chromium(III) propionate-brine-polyacrylamide resulted in the development of high residual resistance factors (RRF) in the Berea sandstone cores. Representative laboratory runs are summarized in Table I:

TABLE I (Laboratory Scale Runs)
Nitrite/Dichromate System in Aqueous Propionic Acid
for Preparation of Chromium (III) Propionate

| Run[a] No. | Components Charged[b] | | | | Reaction Temp. °C. | Reaction Time (Hrs.) |
|---|---|---|---|---|---|---|
| | $K_2Cr_2O_7$ | $CH_3CH_2CO_2H$[c] | $H_2O$[b] | $NaNO_2$[b] | | |
| 1 | 22.05 | 140 | 60 | 16.05 | 70 | 2 |
| 2 | 22.05 | 119 | 51 | 16.05 | 70 | 2 |
| 3 | 22.05 | 119 | 51 | 16.05[d] | 70 | 1.5 |
| 4 | 22.05 | 119 | 51 | 16.05 | 80 | 1.5 |

TABLE I-continued (Laboratory Scale Runs)
Nitrite/Dichromate System in Aqueous Propionic Acid
for Preparation of Chromium (III) Propionate

| Run[a] No. | Components Charged[b] | | | | Reaction Temp. °C. | Reaction Time (Hrs.) |
|---|---|---|---|---|---|---|
| | $K_2Cr_2O_7$ | $CH_3CH_2CO_2H$[c] | $H_2O$[b] | $NaNO_2$[b] | | |
| 5 | 22.05 | 119 | 51 | 16.05 | 80 | 1 |
| 6 | 22.05 | 119 | 51 | 16.05 | 90 | 1 |

[a]All runs employed a 3.11 to 1 molar ratio of $NaNO_2:K_2Cr_2O_7$. The stoichiometric molar ratio is 3:1.
[b]Grams.
[c]The molarity of the aqueous propionic acid solution was 9.46.
[d]The $NaNO_2$ was dissolved in water and added as a solution in Run 3. The amounts shown above are the grams of $NaNO_2$.

Each run shown in Table I gave a green-colored transparent solution which was suitable for gelling polyacrylamide and therefore useful in permeability contrast correction operations to enhance oil recovery.

Referring to the results in Table I, attention is called to Run 3 wherein the $NaNO_2$ was added as a solution. The $NaNO_2$ was added as a solid in Runs 1, 2, 4, 5, and 6. Since all the runs gave active chromium(III) propionate solutions, it is evident that the $NaNO_2$ can be added as a solid or more conveniently added as aqueous solutions. Runs 1, 2, and 3 demonstrate that at 70° C., a digestion period of 1.5 to 2 hours is sufficient to prepare the chromium(III) propionate solution. Runs 4, 5, and 6 demonstrate that at the slightly higher temperatures of 80° C. or 90° C., that a digestion period of only 1 hour is sufficient to prepare the chromium(III) propionate solution.

Example II

This Example presents typical 5-gallon reactor runs which produced "active" chromium(III) propionate solutions. The successful 5-gallon reactor runs were scaled-up from typical laboratory procedures. The product solutions contained no residual dichromate and produced no insoluble material on dilution with water. The visible spectra of these solutions exhibited absorbance maxima at 435 nm and 580 nm. These solutions were effective for gelling polyacrylamide solutions in bulk gel tests. The 5-gallon reactor runs are summarized in Table II:

TABLE II (5-Gallon Reactor Runs)
Nitrite/Dichromate System in Aqueous Propionic Acid
for Preparation of Chromium (III) Propionate

| Run No. | Components Charged[a] | | | | Reaction Temp. °C. | Reaction Time (Hrs.) |
|---|---|---|---|---|---|---|
| | $K_2Cr_2O_7$ | $CH_3CH_2CO_2H$ | $H_2O$ | $NaNO_2$ | | |
| 7 | 1386.95[b] | 7485.10[c] | 1949.90 | 1018.98[d] | 80 | 2 |
| 8 | 1386.95[b] | 7485.10[c] | 1949.90 | 1018.98[d] | 80 | 1.5 |

[a]Grams
[b]This amount of $K_2Cr_2O_7$ corresponds to a 62.9-fold "scale-up" of the runs in Table I, i.e., 22.05 × 62.9 equals 1386.95 grams of $K_2Cr_2O_7$.
[c]This amount of $CH_3CH_2CO_2H$ corresponds to a 62.9-fold "scale-up" of Runs 2–6 in Table I, i.e., 119 × 62.9 equals 7485.1 grams of propionic acid.
[d]This amount of $NaNO_2$ was dissolved in 1258 grams of $H_2O$ and added as an aqueous solution. This represents a 62.9-fold "scale-up" based on 16.2 g $NaNO_2$, i.e., 62.9 × 16.2 equals 1018.98 grams.

Referring to the results in Table II, it is evident that digestion at 80° C. for either 1 or 2 hours is sufficient to prepare "active" chromium(III) propionate solution. These runs demonstrated that a simple "scale-up" from the 500 mL reactor to a 5-gallon reactor was successful.

Example III

Employing the usual batch stirred process, the formation of the chromium(III) propionate complex usually processes through a somewhat sludgy intermediate before becoming the desired clear clean green complex solution.

However, it has been our observation, that if, instead of using a batch-stirred tank, a circulating pump coupled with a batch vessel is employed, and using a high circulating pump rate while heating to the desired reaction temperature, that the preparation of the chromium-(III) propionate complex never appears to process through a sludgy intermediate. In addition, solids do not appear, and the digestion rate to produce the active product usually is reduced from such as about 1 hour to about 0.5 hour. Below is a comparison between runs made in a stirred batch reactor versus a circulating pump batch system:

TABLE III

| Run No. | Potassium Dichromate grams | Sodium Nitrite grams | Propionic Acid grams | Water grams | Reaction Time Hrs. | Reaction Temp. °C. | Agitation | Visible Peaks | Solids |
|---|---|---|---|---|---|---|---|---|---|
| 9 | 22.05 | 16.05 | 119 | 51 | 1.0 | 80 | Stirring 300 rpm | 436 nm 580 nm | none |
| 10 | 22.05 | 16.50 | 119 | 51 | 0.5 | 80 | Pumping 1440–2340 mL per min. for a total vol. of 171 mL | 436 nm 580 nm | none |

Example IV

This example describes a large scale run in a 100 gallon reactor employing a circulating pump (see FIG. 1) to prepare three 55-gallon drum quantities of the chromium(III) propionate solution suitable for crosslinking polymeric viscosifiers in permeability contrast corrections in enhanced oil recovery operations.

The reactor was charged with 71.4 lbs. water and 83.63 lbs. of sodium dichromate dihydrate (0.28 lb. mole of $Na_2Cr_2O_7.2H_2O$). This mixture was stirred for about 15 minutes at ambient temperature to effect complete solution of the dichromate. To this dichromate solution was added with stirring 249.15 lbs. or propionic acid. This aqueous solution was about 75 weight percent propionic acid (based on the combined weight of water and propionic acid). The molar ratio of propionic acid to $Na_2Cr_2O_7$ was about 12:1. This aqueous solution of sodium dichromate and propionic acid was stirred and cooled to approximately 50° F.–60° F. before commencing the slow addition of an aqueous sodium nitrite solution. The sodium nitrite solution was prepared by dissolving 58.8 lbs. (0.85 lb. mole) $NaNO_2$ in 74.9 lbs. of water. The sodium nitrite solution was added slowly to the reaction mixture through the circulating pump with efficient cooling of the system so that the temperature of the circulating reaction mass did not exceed 80° F. After all of the sodium nitrate solution had been added, the reaction mixture was stirred vigorously for an additional 15 minutes.

The circulating reaction mixture was heated to about 180° F. and maintained in the temperature range of 176° F. to 186° F. for a period of one hour. At this point in the procedure samples of the reaction mixture were tested for the presence of residual dichromate and polymer as described hereinabove. If these tests showed residual dichromate and/or polymer then the reaction mass was heated to about 180° F. and testing was continued at 30-minute intervals until both tests were "negative".

The reaction mixture was cooled to ambient temperature and 93.6 lbs. of 35 weight percent aqueous hydrochloric acid was added through the circulating pump. During the addition of this added acid ligand, the reaction mass temperature was maintained at less than 90° F. This mixture was stirred for 15 minutes at ambient temperature, and then heated with stirring for one hour in the temperature range of 176° F. to 186° F. The mixture was tested as before for residual dichromate and polymer. Again, if these tests were "negative", the reaction mixture was cooled to less than 90° F., diluted with 20 gallons of water and stirred for 5 to 10 minutes.

A charge of 20 lbs. aqueous ammonium hydroxide (21.6 weight percent $NH_3$) was slowly added to the system while keeping the temperature under 100° F., and, after this addition, the reaction mixture was stirred for a further 15 minutes. This addition of ammonium hydroxide was used to adjust the pH into the range of 3 to 4.

The resulting reaction mass was pumped into each of three 55 gallon drums so that each drum was half full. To each drum was added sufficient water to bring the volume in each drum to the 55 gallon capacity. This chromium(III) propionate solution was suitable for crosslinking polymeric viscosifiers in enhanced oil recovery operations.

EXAMPLE V

Various chromium(III) compounds were studied as chromium sources for chromium(III) propionate. Chromium(III) oxide was eliminated because of its insolubility in propionic acid and water. Chromium(III) acetate was eliminated because of the greater coordination affinity of the acetate versus the desired propionate. Chromium(III) nitrate appeared to be the only common chromium(III) compound which did not have major drawbacks from a chemical standpoint. Chromium(III) nitrate was stirred in the presence of propionic acid, propionic anhydride, and propionic anhydride and ethanol (all in approximately 30 percent by weight water.) Only chromium(III) nitrate in an ethanol, propionic anhydride, and water mixture yielded a green solution. This solution, through, showed a slightly different absorbance peak maxima in the visible spectra when compared to either the active dichromate-nitrate route or the dichromate-bisulfite route to chromium propionate. Chromium(III) nitrate is too expensive for large-scale commercial usage in any event.

Polymers

Polymers suitable for use with the propionate-complexed chromium(III) solutions of our invention are those capable of gelling in the presence of polyvalent metal ion crosslinking agents within a gelation pH range. Polymers suitable for use in this invention, i.e., those capable of gelling in the presence of crosslinking agents within a gelation pH range, include biopolysaccharides, cellulose ethers, and the acrylamide-based polymers. These should be polyanionic wherein at least a portion of the anionic sites should be carboxylate and/or carboxylic acid groups.

Suitable polymers preferably have pendant carboxylate groups or, also preferably, carboxylic acid groups which provide sites for crosslinking with polyvalent metal cations such as chromium(III) available, e.g., from the dissociation of $Cr^{+3}$ from sequestered chromium in chromium(III) propionate.

Bipolysaccharides possess "natural" sites for crosslinking such as oxygen-containing functional groups such as $-OH$ and possibly $-CO_2H$. Cellulose ether-based polymers likewise preferably contain pendant anionic sites such as in carboxymethyl cellulose (CMC) to be effective for crosslinking, viz, $-CH_2CO_2^-$.

Theoretically, one would not expect a completely nonionic polymer to crosslink, i.e.:

polyacrylamide (0% hydrolysis)    poly(N—vinyl-2-pyrrolidone)

since, e.g., there are no carboxylate or carboxylic acid or other groups such as —OH present for crosslinking.

In general, there are two primary methods to prepare "crosslinkable" polymer, e.g. (1) The hydrolysis of functional groups to generate carboxylate or carboxylic acid groups and (2) the polymerization of monomers at least one of which bears a carboxylate or carboxylic acid group:

(1) Partial hydrolysis of functional groups on a polymer substrate can give rise to carboxylate (pH>7) or carboxylic acid sites (pH<7), e.g.:

For example, a 50/50 poly(N—vinyl-2-pyrrolidone-co-acrylamide) copolymer (VP/Am)

↓ H₂O (aging) (OH⁻ or H⁺)

poly(N—vinyl-2-pyrrolidone-co-acrylamide-co-acrylic acid) (VP/Am/AA) or (VP/Am/NaAA).

However, such aging can require a long period of time, which is commercially desirable.

(2) Polymerization of monomers at least one of which possesses a carboxylic acid or carboxylate moiety:

A monomer such as sodium acrylate is used in the polymerization to prepare acrylate modified polymer directly, e.g., the terpolymerization of N-vinyl-2-pyrrolidone, acrylamide, and sodium acrylate would yield poly(N-vinyl-2-pyrrolidone-co-acrylamide-co-sodium acrylate)(VP/Am/NaAA).

Suitable crosslinkable cellulose ethers include those disclosed in U.S. Pat. No. 3,727,688 (incorporated herein by reference). Particularly preferred cellulose ethers include carboxymethylhydroxyethyl cellulose (CMHEC) and carboxymethyl cellulose (CMC). Each of these cellulosic ether polymers possess pendant carboxymethyl groups (—CH₂CO₂⁻) introduced, e.g., by the carboxymethylation of cellulosic —OH groups with chloroacetic acid under alkaline conditions as is well known in the art.

Suitable biopolysaccharides include those disclosed in U.S. Pat. No. 4,068,714 (incorporated herein by reference). Particularly preferred of these is polysaccharide B-1459, a biopolysaccharide produced by the action of *Xanthomonas campestris* bacteria, and commercially available in various grades under the trademark Kelzan ® (Kelco Company, Los Angeles, Calif.).

Among the suitable acrylamide-based polymers are those disclosed in U.S. Pat. No. 3,749,172 (incorporated herein by reference). Particularly preferred are the so-called partially hydrolyzed acrylamide-based polymers possessing pendant carboxylate groups through which crosslinking can take place. Thermally stable copolymers of acrylamide, such as poly(N-vinyl-2-pyrrolidone-co-acrylamide) and poly(sodium 2-acrylamido-2-methyl-1-propanesulfonate-co-acrylamide), are particularly preferred for applications in high salinity environments at elevated temperatures. Selected terpolymers also are useful in the present process, such as terpolymers derived from acrylamide and N-vinyl-2-pyrrolidone comonomers with lesser amounts of termonomers such as acrylic acid, sodium acrylate, vinyl acetate, vinylpyridine, styrene, methyl methacrylate, and the like. Sodium acrylate modified acrylamide-based polymers such as poly(N-vinyl-2-pyrrolidone-co-acrylamide-co-sodium 2-acrylamido-2-methyl-1-propanesulfonate-co-sodium acrylate)(30/10/55/5 wt/wt/wt/wt) are particularly preferred.

Other miscellaneous polymers suitable for use in the present invention include partially hydrolyzed polyacrylonitrile, polystyrene sulfonate, lignosulfonates, methylolated polyacrylamides, and the like.

In general, the gelation pH range is a pH range of about 3 to 7. It is recognized that this range may vary somewhat for various polymers, or polymer-metal cation combinations or concentration relationships. The specific gelation pH range is readily determinable for a given or specific polymer or polymer-metal cation combination by testing same with additions of acid and following the resulting pH change until gelation is observed.

Presently preferred are the acrylamide based polymers, particularly the polyacrylamides and the partially hydrolyzed polyacrylamides, preferably in conjunction with $Cr^{3+}$ as the metal cation, presently most preferably as the instant chromium(III) propionate solution.

The concentration or water-thickening amount of the water-soluble/dispersible polymer in the aqueous solution/dispersion can range widely and be as suitable and convenient for the various polymers, and for the degree of gelation needed for particular strata. Generally, the concentration of polymer in its aqueous solution/dispersion (before admixing with crosslinking components or ester) is about 1,000 to 20,000 ppm, preferably about 2,000 to 5,000 ppm.

Any suitable procedures for preparing the aqueous admixtures of the crosslinking polymer can be used. Some of the polymers may require particular mixing conditions, such as slow addition of finely powdered polymer into the vortex of stirred water, alcohol pre-wetting, protection from air (oxygen), preparation of stock solutions from fresh rather than salt water, or the like, as is known for such polymers.

Generally, the ratio of number of polyvalent metal cations to crosslinkable side groups on the polymeric viscosifier will vary over the broad range of about 10:1 to 1:10, presently preferably about 5:1 to 1:1.

Conveniently, the polymer can be dispersed in a given amount of water, and to the dispersion then added the desired amounts of a solution or dispersion of the sequestered polyvalent metal cation crosslinking agent.

After admixing with the aqueous solution of the crosslinking agent, the polymer concentration generally will be of the order of about 500 to 10,000 ppm, more usually about 1,000 to 2,500 ppm.

Compositions for Injection

The amount of crosslinking agent used depends largely on the amounts of polymer in solution. Lesser amounts of polymer require lesser amounts of crosslinking agent, and vice-versa. Further, it has been found that for a given concentration of polymer that increasing the amount of crosslinking agent generally substantially increases the formation plugging effectiveness.

The chromium(III) propionate solution and the polymer solution can be pre-mixed on the surface and then injected as a slug. The solutions can be kept separate and can be mixed together by inter-mixing devices or valves as injection proceeds, where desired. Alternatively, a sequential injection of aqueous polymer-aqueous chromium(III) propionate-aqueous polymer can also be used for permeability contrast correction.

Amount of Gelable Composition

The total quantity of gelable treating composition employed can be expressed in terms of the pore volume of the area to be treated. For example, if a region (one or more stratum or portion thereof) to be treated is taking upwards of 80 volume percent of the volume of injected fluid, a packer can be set to direct the treating composition into this zone. The volume of treating composition can vary widely, depending on the effects desired, but generally from about 100 percent to 120 percent of the pore volume of the zone to be treated with the upper limit being governed merely by the practical limitations of pumping expense and chemical costs.

Preflush (Optional)

Prior to employment of the gelable compositions, the strata can be subjected to a conditioning preflush step.

The optional preflush employs aqueous solution with a lower level of hardness and/or total dissolved solids (tds) than that of the stratum connate water, of preferably containing substantially no hardness cations though it may be saline. The purpose of the preflush is to alter the salinity of the connate water by flushing the formation, generally with about one to three times the pore volume of the zone to be treated.

Since it is known that enhanced oil recovery chemicals such as surfactants and polymeric viscosifiers are adsorbed and/or precipitated to a greater extent in the presence of electrolytes and hardness cations in particular, the preflush alleviates this potential problem by sweeping out a certain fraction of such electrolytes. A typical NaCl preflush brine contains, e.g., on the order of about 0.2 to 2 weight percent total dissolved solids.

Spacer Solution

Optionally, a spacer solution slug of a sequestrant can be employed, within the aqueous polymer-aqueous chromium propionate-aqueous polymer sequential repeating cycle, with or without brine spaces. The sequestrant solution preferably is aqueous sodium propionate, but can be an aqueous alkaline metal salt solution of a sequestering anion such as citrate, acetate, tartrate, gluconate, nitriloacetate, any of the polyphosphates of sequestering character, ethylenediaminetetraacetic acid, alone, in admixture, or in admixture with propionate. The spacer sequestrant concentration can be as convenient depending on water solubility. The volume of spacer solution employed can be similar to the suggested amount of preflush employed.

Aqueous Drive Fluid

The aqueous drive generally follows the permeability contrast correction process of our invention. The aqueous drive employs available field brines and/or fresh water if the latter is obtainable.

The aqueous drive, since it follows the gelation treatment, is diverted to the (formerly) relatively less permeable oil-rich zones since the permeability contrast correction process shows or substantially prevents the flow of aqueous drive fluid through the (originally) more permeable but oil-poor zones (so-called thief zones). A successful permeability contrast correction operation generally is signaled at the production well by a lowering of the water/oil ratio in the produced fluid.

Subsequent to the permeability contrast correction, the water/oil ratio may gradually increase again after prolonged injection of the drive water. A gelation retreatment of the formation may be considered appropriate, if desired.

The disclosure, including data, has illustrated the value and effectiveness of our invention. The Examples, the knowledge and background of the field of the invention and the general principles of chemistry and of other applicable sciences have formed the bases from which the broad descriptions of our invention including the ranges of conditions and the generic groups of operant components have been developed, and formed the bases for our claims here appended.

We claim:

1. A method of producing a stabilized chromium(III) propionate solution which comprises the steps of:
    (a) admixing a propionic acid source selected from propionic acid and propionic anhydride with water thereby forming an aqueous solution of propionic acid containing 50 to 70 weight percent propionic acid;
    (b) adding to said aqueous propionic acid a chromium(VI) source selected from the group consisting of chromium(VI) oxide and alkali metal and ammonium dichromates and chromates thereby forming a solution of said chromium(VI) source in said aqueous propionic acid employing a molar ratio of at least about 4:1 propionic acid:chromium and
    (c) adding to said solution of chromium(VI) source in aqueous propionic acid a nitrite source employing sufficient nitrite source selected from the group consisting of alkali metal and ammonium nitrites to effectively reduce chromium(VI) to chromium(III) allowing sufficient time at sufficient temperature to produce a clear green solution of stabilized chromium(III) propionate; and
    (d) adding to said stabilized chromium(III) propionate solution an additional acid selected from the group consisting of propionic acid, hydrochloric acid, acetic acid and acetic anhydride to adjust total acidity to at least about an 11:1 molar ratio of acid:chromium.

2. The process according to claim 1 wherein said chromium(VI) source is potassium dichromate or sodium dichromate and said nitrite source is sodium nitrite.

3. The process according to claim 2 wherein said propionic acid source is propionic acid.

4. The process of claim 3 wherein said additional acid is propionic acid.

5. The process of claim 4 wherein said additional acid is hydrochloric acid.

6. The process of claim 4 wherein said additional acid is acetic acid.

7. The process of claim 1 employing in said step (b) propionic acid in a molar ratio range of about 4:1 to 45:1 propionic acid:chromium.

8. The process of claim 1 employing a reaction time of about 0.5 to 24 hours, and a reaction temperature of about 60° C. to 100° C.

9. The process of claim 1 employing a loop admixing procedure.

10. The stabilized chromium(III) propionate solution prepared by the process which comprises the steps of:
 (a) admixing a propionic acid source selected from the group consisting of propionic acid and propionic anhydride with water thereby forming an aqueous propionic acid solution containing 50 to 70 weight percent propionic acid,
 (b) adding to said aqueous propionic acid a chromium(VI) source selected from the group consisting of chromium(VI) oxide and alkali metal and ammonium dichromates and chromates thereby forming a solution of said chromium(VI) source in said aqueous propionic acid employing a molar ratio of at least about 4:1 propionic acid:chromium,
 (c) adding to said solution of chromium(VI) source in aqueous propionic acid, a nitrite source selected from alkali metal and ammonium nitrites, employing sufficient nitrite source to effectively reduce said chromium(VI) source to chromium(III) and allowing sufficient time at sufficient temperature to produce a clear green solution of stabilized chromium(III) propionate; and
 (d) adding to said stabilized chromium(III) propionate solution an additional acid selected from the group consisting of propionic acid, acetic acid, acetic anhydride and hydrochloric acid to adjust total acidity to at least about an 11:1 molar ratio of acid:chromium.

11. The stabilized chromium(III) propionate solution of claim 10 wherein the additional acid is other than propionic acid and is added in said step (d).

12. The stabilized chromium(III) propionate solution of claim 10 wherein said chromium(VI) source is potassium dichromate or sodium dichromate.

13. The stabilized chromium(III) propionate solution of claim 12 wherein said nitrite source is sodium nitrite.

14. The stabilized chromium(III) propionate solution of claim 13 wherein said propionate source is propionic acid.

15. The stabilized chromium(III) propionate solution of claim 14 wherein said additional acid is selected from the group consisting of hydrochloric acid, acetic acid, and acetic anhydride wherein said additional acid is added in said step (d).

16. The stabilized chromium(III) propionate solution of claim 15 wherein said additional acid is hydrochloric acid.

17. The stabilized chromium(III) propionate solution of claim 15 wherein said additional acid is acetic acid.

18. The stabilized chromium(III) propionate solution of claim 10 employing in said step (b) propionic acid in a molar ratio range of about 4:1 to 45:1 propionic acid:chromium.

19. The stabilized chromium(III) propionate solution of claim 10 employing in said step (b) propionic acid in a molar ratio range of at least about 4:1 propionic acid:chromium, and in step (c) an additional acid, selected from hydrochloric acid and acetic acid, to bring the total acidity to at least about an 11:1 molar ratio of acid:chromium.

* * * * *

UNITED STATES PATENT AND TRADEMARK OFFICE
CERTIFICATE OF CORRECTION

PATENT NO. : 4,636,572

DATED : January 13, 1987

INVENTOR(S) : Paul S. Hudson et al

It is certified that error appears in the above-identified patent and that said Letters Patent is hereby corrected as shown below:

Column 18, claim 14, line 2, "propionate" should read --- propionic acid ---.

Signed and Sealed this

Twenty-fourth Day of March, 1987

Attest:

DONALD J. QUIGG

Attesting Officer     Commissioner of Patents and Trademarks